(12) United States Patent  
Johnson et al.

(10) Patent No.: US 10,660,543 B2
(45) Date of Patent: *May 26, 2020

(54) BREATHING DETECTION APPARATUS

(71) Applicant: Bohnas Innovations LLC, Coeur d'Alene, ID (US)

(72) Inventors: Casey Johnson, Coeur d'Alene, ID (US); Doran Thomas, Post Falls, ID (US); Greg Bauer, Post Falls, ID (US)

(73) Assignee: Bohnas Innovations LLC, Coeur d'Alene, ID (US)

( * ) Notice: Subject to any disclaimer, the term of this patent is extended or adjusted under 35 U.S.C. 154(b) by 279 days.

This patent is subject to a terminal disclaimer.

(21) Appl. No.: 15/694,415

(22) Filed: Sep. 1, 2017

(65) Prior Publication Data

US 2018/0020949 A1    Jan. 25, 2018

Related U.S. Application Data

(63) Continuation of application No. 14/664,611, filed on Mar. 20, 2015, now Pat. No. 9,808,182.

(51) Int. Cl.
*A61B 5/08*    (2006.01)
*A61B 5/097*    (2006.01)
(Continued)

(52) U.S. Cl.
CPC ............ *A61B 5/097* (2013.01); *A61B 5/0836* (2013.01); *A61B 5/7405* (2013.01);
(Continued)

(58) Field of Classification Search
CPC ..... A61B 5/097; A61B 5/0836; A61B 5/7405; A61M 16/085; A61M 16/0666;
(Continued)

(56) References Cited

U.S. PATENT DOCUMENTS 3,643,660 A    2/1972  Hudson et al.
4,201,205 A    5/1980  Bartholomew
(Continued)

FOREIGN PATENT DOCUMENTS

EA          004670 B1     6/2004
WO    WO2006106328 A1    10/2006

OTHER PUBLICATIONS

"Biomarkers and Measurement of Risks: Concepts and Principles", Gigienicheskie kriterii sostoyaniya okruzhayuschei sredy 155. Vsemirnaya organizatsiya zdravookhraneniya, Aheneva, 1996, p. 50, lines 11-41, p. 51, lines 1-29.

(Continued)

*Primary Examiner* — Navin Natnithithadha
*Assistant Examiner* — Andrey Shostak
(74) *Attorney, Agent, or Firm* — Lee & Hayes, P.C.

(57) ABSTRACT

An apparatus including a tubular channel having a pathway extending between a proximal end and a distal end of the tubular channel. The proximal end is configured to connect directly or indirectly to an end tidal $CO_2$ monitor. The distal end has an opening. The apparatus further includes a detection member including a chamber disposed in fluid communication with the pathway of the tubular channel such that gas entering the tubular channel via the opening on the distal end passes into the chamber. A detection element is disposed within the chamber and includes a component that is sensitive to one or more systemic biomarkers such that, upon exposure to a predetermined concentration level of the one or more systemic biomarkers contained in the gas, a state of the detection element experiences a permanent alteration and the detection member indicates that the predetermined concentration level of the one or more systemic biomarkers is present in the gas.

18 Claims, 9 Drawing Sheets

(51) Int. Cl.
*A61B 5/083* (2006.01)
*A61B 5/00* (2006.01)
*A61M 16/08* (2006.01)
A61M 16/06 (2006.01)
A61M 16/04 (2006.01)
A61M 16/16 (2006.01)
A61M 25/02 (2006.01)

(52) U.S. Cl.
CPC ....... *A61M 16/085* (2014.02); *A61M 16/0666* (2013.01); *A61M 16/0672* (2014.02); *A61M 16/161* (2014.02); *A61M 25/02* (2013.01); *A61M 2016/0413* (2013.01); *A61M 2025/024* (2013.01); *A61M 2025/028* (2013.01); *A61M 2025/0293* (2013.01); *A61M 2205/0227* (2013.01); *A61M 2205/273* (2013.01); *A61M 2205/581* (2013.01); *A61M 2205/587* (2013.01); *A61M 2205/588* (2013.01); *A61M 2230/432* (2013.01)

(58) Field of Classification Search
CPC ............ A61M 16/161; A61M 16/0672; A61M 2016/0413; A61M 2230/432; A61M 2205/588; A61M 2205/587; A61M 2205/581; A61M 2205/273; A61M 2205/0227; A61M 25/02
See application file for complete search history.

(56) References Cited

U.S. PATENT DOCUMENTS

| | | | |
|---|---|---|---|
| 5,474,060 A | 12/1995 | Evans | |
| 5,849,594 A | 12/1998 | Balderson et al. | |
| 6,247,470 B1 | 6/2001 | Ketchedjian | |
| 6,502,573 B1 * | 1/2003 | Ratner | A61M 16/208 128/202.22 |
| 7,418,965 B2 | 9/2008 | Fukunaga et al. | |
| 7,500,482 B2 | 3/2009 | Biederman | |
| 7,640,932 B2 | 1/2010 | Curti et al. | |
| 8,720,445 B2 | 5/2014 | Cain et al. | |
| 2003/0229295 A1 * | 12/2003 | Houde | A61F 2/013 600/585 |
| 2004/0163648 A1 | 8/2004 | Burton | |
| 2008/0260302 A1 | 10/2008 | Martinez | |
| 2008/0275427 A1 | 11/2008 | Sage | |
| 2010/0317956 A1 | 12/2010 | Kartush | |
| 2011/0199220 A1 | 8/2011 | McAlister | |
| 2011/0230700 A1 | 9/2011 | Sing et al. | |
| 2011/0257550 A1 | 10/2011 | Choi | |
| 2011/0297696 A1 | 12/2011 | Casares | |
| 2012/0271187 A1 | 10/2012 | McNeill | |
| 2013/0338521 A1 | 12/2013 | Thompson et al. | |
| 2013/0345587 A1 | 12/2013 | Colman | |
| 2014/0018691 A1 * | 1/2014 | McNeill | A61M 16/04 600/532 |
| 2014/0065602 A1 | 3/2014 | Milton et al. | |
| 2015/0099993 A1 * | 4/2015 | Weaver | A61M 16/0463 600/531 |
| 2016/0270692 A1 | 9/2016 | Johnson et al. | |

OTHER PUBLICATIONS

Bhavani Shankar Kodali MD, "Capnography in Emergency Tracheal Intubations", retrieved on Apr. 17, 2015 at <<http://www.capnography.com/new/component/content/article?id=277&itemid=152>>, 2 pages.

Office action for U.S. Appl. No. 14/664,611, dated Feb. 9, 2017, Johnson, "Breathing Detection Apparatus", 19 pages.

The PCT Search Report and Written Opinion dated Aug. 11, 2016 for PCT application No. PCT/US2016/023297, 8 pages.

* cited by examiner

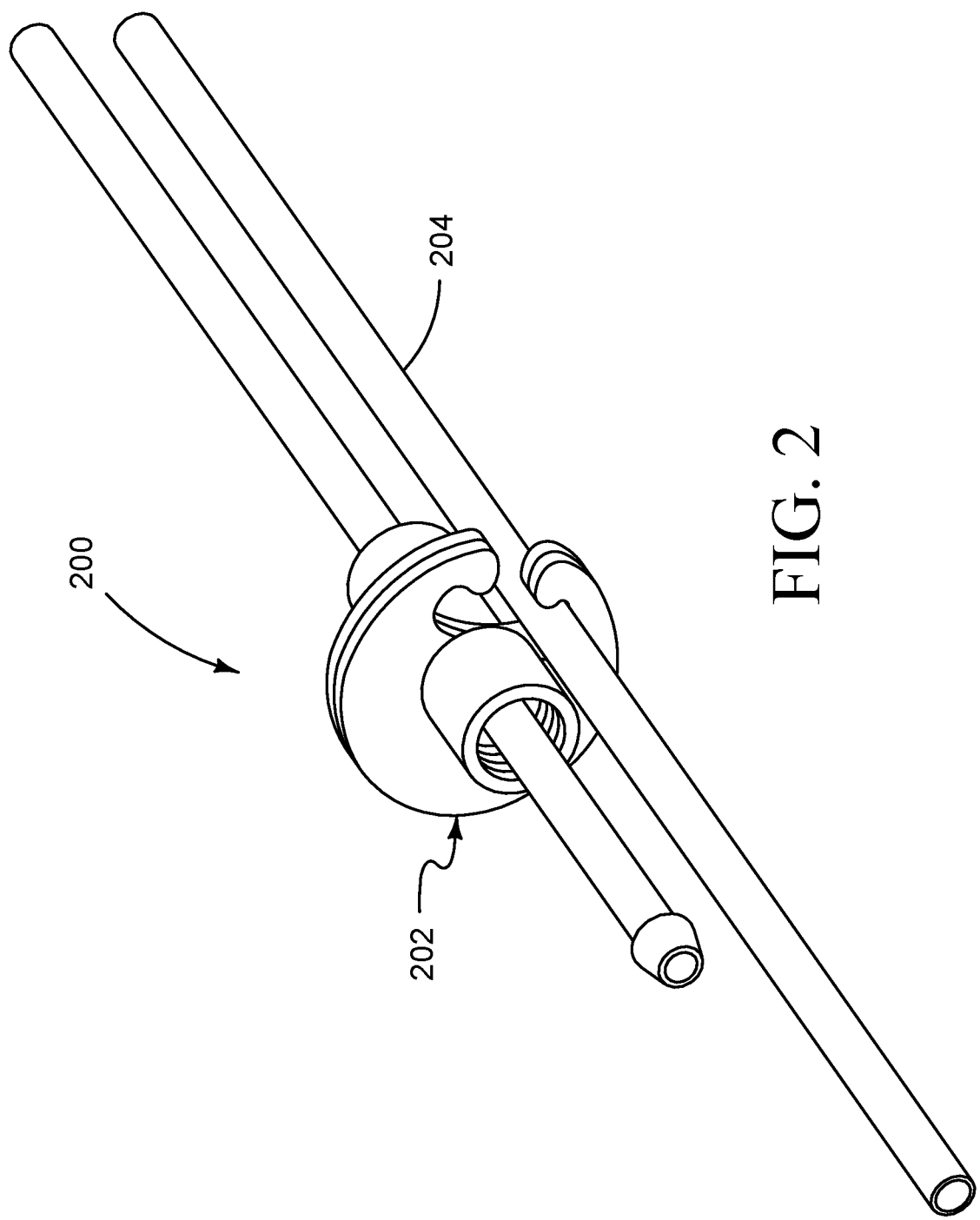

BREATHING DETECTION APPARATUS

CROSS REFERENCE TO RELATED APPLICATIONS

This application is a continuation of, and claims priority to, U.S. application Ser. No. 14/664,611, filed Mar. 20, 2015, incorporated herein by reference.

BACKGROUND

In a medical procedure, during which a patient is sedated or under anesthesia, it is important that the patient's airway and the delivery of gases are monitored closely. There are two main types of anesthesia utilized in caring for patients under anesthesia, namely Monitored Anesthetic Care (MAC) and General Anesthesia (GA). The basic description of "monitoring the airway" is really an oversimplified description of capnography, which is the monitoring of the concentration of end tidal carbon dioxide ("$ETCO_2$") or exhaled carbon dioxide ("$CO_2$") of a patient in order to assess the physiological status and/or determine the adequacy of ventilation during anesthesia.

In the MAC method of capnography, the airway of a patient may be monitored while the patient is wearing a nasal cannula or a simple face mask via which a gas, such as oxygen, is administered to the patient. The face mask may be a plastic, possibly a clear plastic that covers the nose and mouth and is secured to the face by an elastic band around the back of the head. The nasal cannula may be inserted into the nares so that the outflow of oxygen, for example, is inhaled by the patient through the nose.

Alternatively, in GA methods, anesthesia may be accomplished without a nasal cannula or face mask, but instead with a breathing circuit that connects the patient to an anesthetic machine and ventilator. This may be accomplished via an inspiratory and expiratory limb of the breathing circuit connected to the patient at a breathing device that terminates at or about the tracheal opening of the patient's lungs.

In some instances, the effects of sedatives, narcotics, and the majority of general anesthetics decrease respiratory drive and can cause brief or prolonged periods of apnea. Because of such a situation, the implementation of capnography increases the margin of safety for delivery of anesthesia.

BRIEF DESCRIPTION OF THE DRAWINGS

The Detailed Description is set forth with reference to the accompanying figures. In the figures, the left-most digit(s) of a reference number identifies the figure in which the reference number first appears. The use of the same reference numbers in different figures indicates similar or identical items. Furthermore, the drawings may be considered as providing an approximate depiction of the relative sizes of the individual components within individual figures. However, the drawings are not to scale, and the relative sizes of the individual components, both within individual figures and between the different figures, may vary from what is depicted. In particular, some of the figures may depict components as a certain size, while other figures may depict the same components on a larger scale for the sake of clarity.

FIG. 2 illustrates an isometric view of an example breathing detection apparatus attached to a nasal cannula.

DETAILED DESCRIPTION

Overview

Figure 1A:
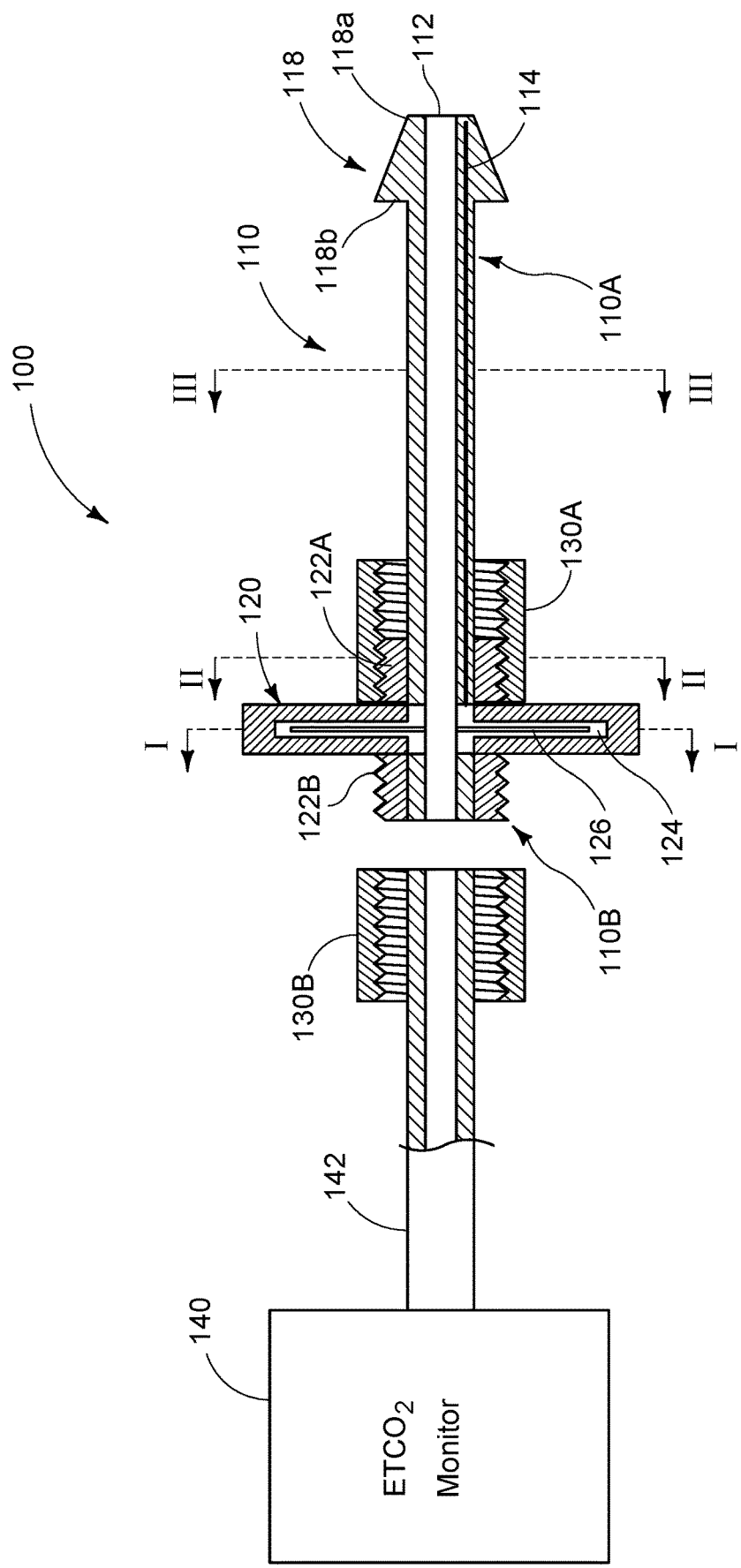
FIG. 1A illustrates a side cross-sectional view of an example of a breathing detection apparatus.

This disclosure is directed to an apparatus that may be used in monitoring the presence of and/or concentration of a systemic biomarker, such as $ETCO_2$ or exhaled $CO_2$ of a patient in order to assess the physiological status and/or determine the adequacy of ventilation during anesthesia. The embodiments are described with specificity in order to meet statutory requirements. However, the description itself is not intended to limit the scope of this patent. Rather, the inventors have contemplated that the claimed invention might also be embodied in other ways, to include different elements or combinations of elements similar to the ones described in this document, in conjunction with other present or future technologies.

The breathing detection apparatus described herein may generally include a tubular channel (also called "a sampling line") and a detection unit that has therein an element sensitive to the systemic biomarkers, which biomarkers may include, for example, $ETCO_2$, nitric oxide, moisture, humidity, temperature, acids, ketones, or other gases, elements, or characteristics found in or associated with exhaled human breath. A biomarker that may be particularly useful is $CO_2$, since the average indoor $CO_2$ levels range from 400-2000 ppm, whereas exhaled $CO_2$ levels range around 38,000 ppm.

The tubular channel permits the flow of exhaled breath to go from the patient to an $ETCO_2$ monitoring device, where the $CO_2$ in the breath exhaled by the patient is monitored for the safety of the patient. With respect to the element in the detection unit that is sensitive to systemic biomarkers, the element is configured such that, upon exposure to a predetermined biomarker, such as $ETCO_2$, an indicator is activated so as to indicate that the element has been exposed and the apparatus has been used. This detection feature notifies the operator of the apparatus, e.g., the anesthesiologist, dentist, or other medical personnel, that the particular ETCO$_2$ monitoring line has been used. As such, the indicator of the detection apparatus may help prevent accidental reuse, which could cause infections due to cross contamination. Further, the detection apparatus may also prevent unintentional and unnecessary waste, which occurs due to operators being unsure whether the apparatus was previously used, in which case, the apparatus is generally thrown away due to uncertainty.

In addition to indicating the prior use of the apparatus, the breathing detection apparatus provides other advantages. Features of the breathing detection apparatus provide versatility in use for various situations, including, but not limited to, being connectable to, for example, a nasal cannula, a face mask, and an endotracheal tube or an adapter therefor. Specifically, the detection unit may include a structural feature (described in detail herein below) that accommodates and secures a nasal cannula thereto. Further, an end of the tubular channel is configured to be secured to either a mask or an anesthesia circuit.

More specifically, the structural features of the breathing detection apparatus allow so that, should it become necessary during a procedure to change between any of the means of providing gas flow to the patient, the various connections are easily accommodated with only minimal effort. For example, if a patient is using a face mask, and it is determined that the patient needs to be intubated, an endotracheal tube may be employed and the breathing detection apparatus may be quickly connected to a compatible port on an adapter interposed between the endotracheal tube and the anesthesia circuit. Likewise, if the patient needs to switch from a face mask to a nasal cannula, or vice-versa, the breathing detection apparatus can be easily removed from one and quickly attached to the other. Thus, the breathing detection apparatus may be used in different situations due to the structure of the apparatus.

Sometimes, using the current methods of practice monitoring ETCO$_2$ during a procedure, issues and problems related to reliability, and potentially dangerous situations occur. Moreover, patients may even alternate breathing through the nose and the mouth. In such an instance, a nasal sampling line will not reliably detect exhaled air coming from the mouth. The breathing detection apparatus of the instant application helps to eliminate or minimize the occurrence of such situations. Namely, the breathing detection apparatus helps to avoid kinking or occlusions of the sampling line (which may be crafted from, for example, intravenous catheter or extension tubing). Further, the apparatus may eliminate the situation where sampling line is taped to the patient's facial skin. In some instances, hypodermic needles are broken during current procedures and used to puncture the face mask so as to insert tubing therein and sample the CO$_2$. In such situations, the patient may be subject to a possible cut or abrasion from the broken end of the needle. Accordingly, the embodiments of the breathing detection apparatus of the instant application, as detailed herein, may provide several advantages over the current methods of monitoring CO$_2$.

Multiple embodiments of an apparatus that may be used to achieve the desired effects of the instant application, including the ability to definitively determine whether a CO$_2$ sampling unit has been used, are described herein below with respect to FIGS. 1A-6. Note that throughout the specification the terms "proximal" and "distal" are used several times. Unless otherwise specified, "proximal" refers to the end of the apparatus 100 that is connectable to an ETCO$_2$ monitor 140, and "distal" refers to the opposite end of the apparatus 100.

Detailed Explanation of the Components in the Figures

FIG. 1A illustrates an example breathing detection apparatus 100 that may include a sampling tube attachment 110, a detection unit 120, and collars 130A, 130B. In order to monitor the level of CO$_2$, the breathing detection apparatus 100 may be connected to the ETCO$_2$ monitor 140 via an extension tube 142.

The sampling tube attachment 110 has a distal end 110A and a proximal end 110B. The proximal end 110B may be connectable directly or indirectly to the ETCO$_2$ monitor 140. The distal end 110A functions as an intake for exhaled breath via a first lumen 112 that is open to the environment at the distal end 110A. In practice, the distal end 110A is positioned in a location with respect to the patient so as to intake the exhaled breath via a suction force, and thereby sample the ETCO$_2$. The position varies depending on the corresponding apparatus, i.e., nasal cannula, face mask, or endotracheal tube, being used to provide gas to the patient. Accordingly, using the apparatus described herein, the concentration of CO$_2$ may be sampled and the status of the patient may be monitored.

One feature of the sampling tube attachment 110, which assists in positioning the distal end 110A near the mouth and/or nose of the patient is a manipulable member 114 disposed adjacent the first lumen 112 in the sampling tube attachment 110. The manipulable member 114 may include a wire, rod, strip, bar, or another section of metal, plastic, ceramic, rubber, or other suitable material, including weather as described below. For example, manipulable member 114 may have a material that is pliable and/or malleable, so as to allow manipulation of the position, shape, and or direction of the extension of the sampling tube attachment 110, with which the manipulable member 114 may be coupled. Thusly, when used in connection with a nasal cannula, the a position of the sampling tube attachment 110 may be manipulated via the manipulable member 114 to be positioned closer to the mouth or the nose of the patient, or therebetween, in order to intake and allow the patient's breath to pass through the first lumen 112 in the sampling tube attachment 110 to the ETCO$_2$ monitor 140.

Figure 1C:
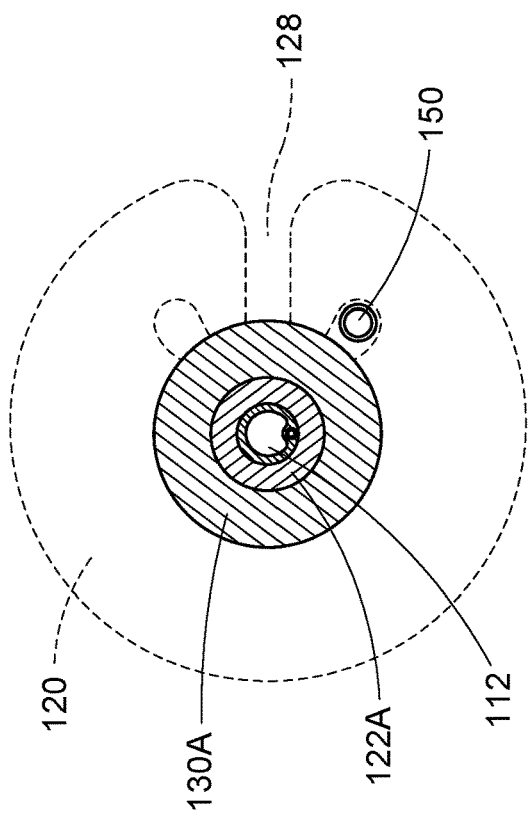
FIG. 1C illustrates another front cross-sectional view at line II-II of a protrusion and collar in front of the chamber of the detection unit of the example breathing detection apparatus in FIG. 1A.
Figure 1D:
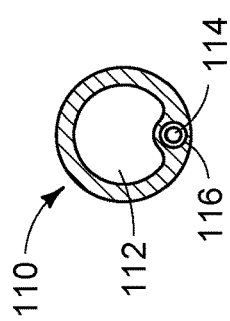
FIG. 1D illustrates another front cross-sectional view at line of a sampling tube attachment in front of the detection unit of the example breathing detection apparatus in FIG. 1A.

Inasmuch as the manipulable member 114 is adjacent the first lumen 112, the manipulable member 114 may be disposed in a second lumen 116 that extends parallel with the first lumen 112, as shown more clearly in FIG. 1D. Alternatively, the manipulable member 114 may be attached directly to an inner surface of the first lumen 112 or an outer surface of the sampling tube attachment 110; or the manipulable member 114 may simply be embedded in the wall of the first lumen 114, as it appears in FIG. 1A. The length of the manipulable member 114 may be such that the manipulable member 114 extends: 1) throughout the entire length of the sampling tube attachment 110; 2) at least along the distal end 110A; or 3) for a portion less than the entire length of the sampling tube attachment 110 and located away from the ends thereof, such as at a middle portion between the distal and proximal ends 110A, 110B.

A tip of the distal end 110A of the sampling tube attachment 110 may have a flange 118. The width of the flange 118 may be tapered. The flange 118 may include an insertion end 118a, which starts at the distal end 110A and may be approximately the same width as the first lumen 112, and an abutting end 118b, which is wider than the insertion end 118a as the flange 118 extends taperingly toward the proximal end 110B, such that the width of the flange 118 is larger at the abutting end 118b at the proximal side than the insertion end 118a at the distal side, as depicted in FIG. 1A.

Figure 4:
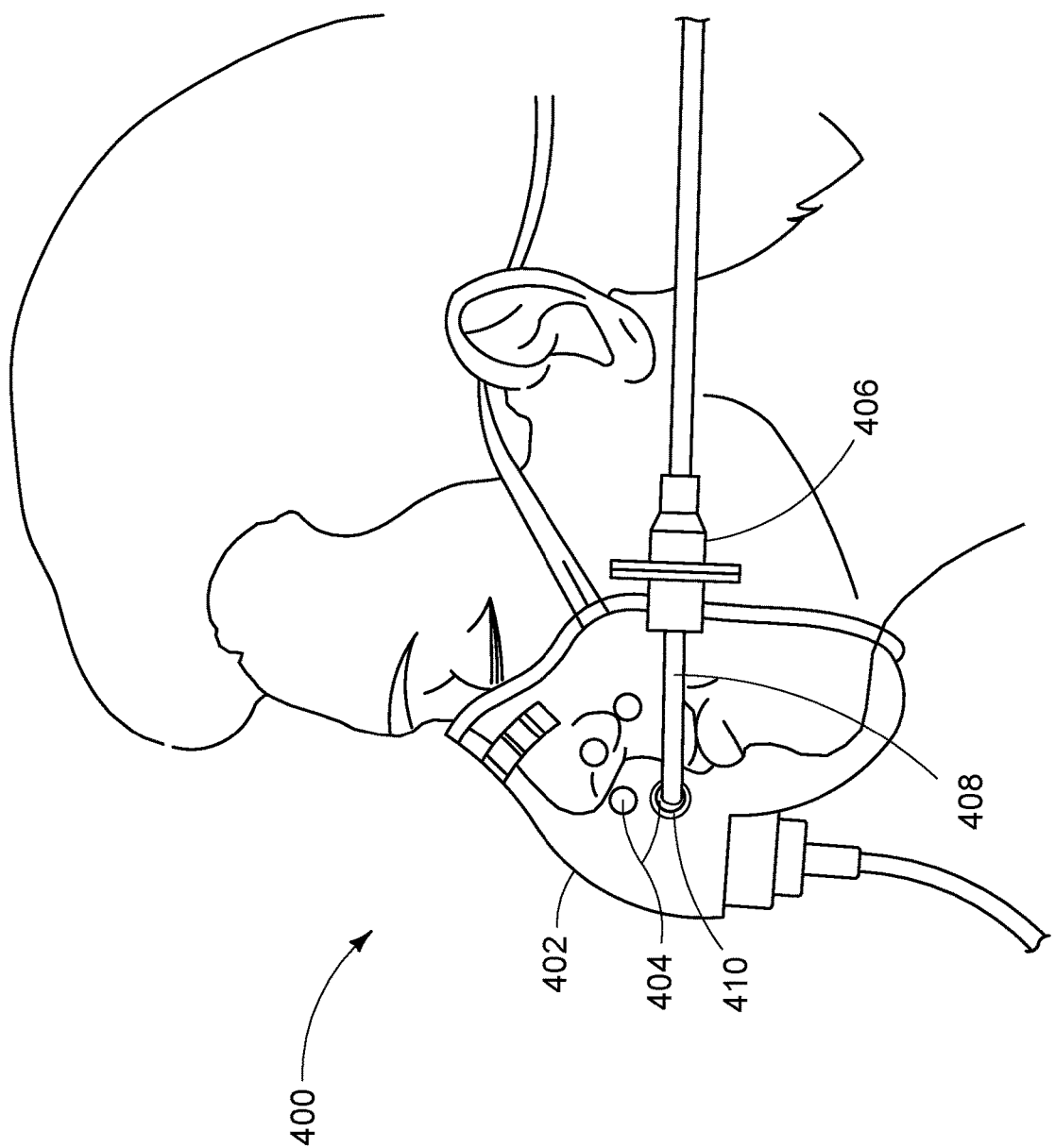
FIG. 4 illustrates a view of an example breathing detection apparatus attached to a face mask.
Figure 5:
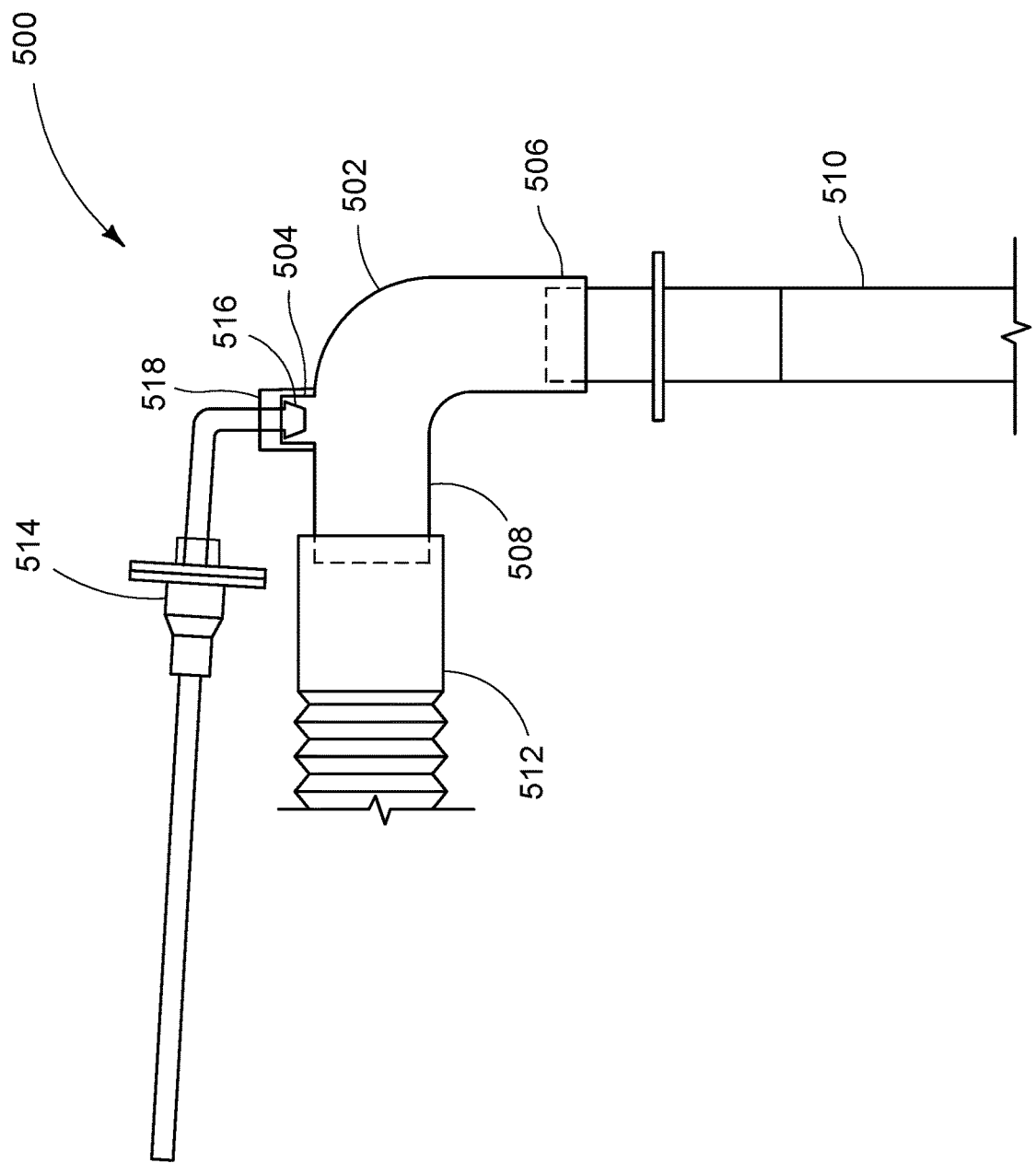
FIG. 5 illustrates an example breathing detection apparatus attached to an adapter on an endotracheal tube.

The abutting end 118b of the flange 118 may be substantially flat and extend in a plane orthogonal to the axis of the first lumen 112, such that, upon inserting the tip of the distal end 110A of the sampling tube attachment 110 into a mask or a port (see, for example, hole 404 on mask 402 in FIG. 4, or port 504 on adapter 502 in FIG. 5), the abutting end 118b abuts an inside surface of the mask or port. (FIGS. 4 and 5 are discussed in greater detail herein below.) Thusly, the abutting end 118b minimizes the chance for accidental extraction of the sampling tube attachment 110 from the mask or port by restricting movement via abutting surfaces.

Turning to the detection unit 120 of the apparatus 100, the detection unit 120 may include a chamber 124 defined by two opposing walls connected at a periphery thereof. The chamber 124 may be sealed from the outside environment with exception of a hole 125 (see FIG. 1B) leading into the chamber 124. The hole 125 may pass through the detection unit 120. Further, the hole 125 may be aligned with the first lumen 112 so as to receive the breath flowing into the first lumen 112.

In an embodiment depicted in FIG. 1A, the detection unit 120 may further include a first protrusion 122A protruding from a wall of the chamber 124, extending toward the distal end 110A of the sampling tube attachment 110, and a second protrusion 122B protruding from the opposite wall of the chamber 124, extending toward the proximal end 110B. As depicted, protrusions 122A and 122B may be tubular bodies having a threaded outer surface. The threaded outer surface of protrusion 122A may connect to collar 130A, which has an inner threaded surface. Likewise, the threaded outer surface of protrusion 122B may connect to collar 130B. Thus, the sampling tube attachment 110 may connect to the monitor 140 via the threaded engagement between protrusion 122B and collar 130B.

The detection unit 120 may further include an element 126 that senses or is sensitive to systemic biomarkers, such as $CO_2$, for example, as discussed above. The element 126 may be configured to experience a permanent change in state upon sensing a predetermined, threshold amount of a biomarker, such as a specific level of $CO_2$ concentration. For the purposes of this application, the term "permanent" means at least until an individual can determine that the apparatus has been used by checking the state of the indicator from element 126. Thus, in an embodiment where the element 126 implements a power source, the term "permanent" would mean until the power source is exhausted. In another embodiment where the element 126 is not electronic, "permanent" means a change of state that is not intermittent or alternating between the original state and the altered state, outside of the intended period of use on a patient. Thus, for example, if the element 126 is a material that changes color, a "permanent" change would be one that would change upon the initial sensing of the threshold amount of the biomarker during the procedure, and which state would not revert to the original state, if ever, until after a length of time after a procedure terminates, during which an individual would have appropriately discarded the used apparatus.

Figure 1B:
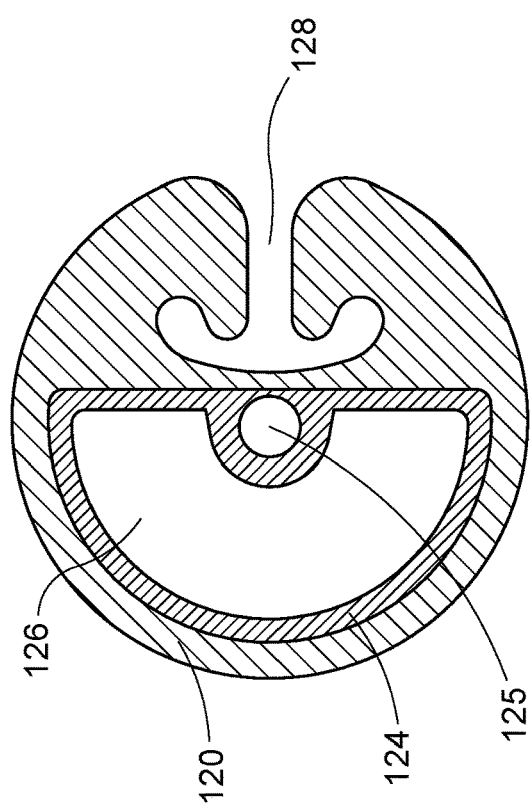
FIG. 1B illustrates a front cross-sectional view at line I-I of the detection unit of the example breathing detection apparatus in FIG. 1A.

The element 126 may be disposed within the chamber 124, as seen in FIGS. 1A and 1B. Alternatively, depending on the embodiment, element 126 may be embedded within walls of the detection unit 120. For example, the element 126 may be a material (e.g., paper or cloth) that is chemically designed to change color or disintegrate upon being exposed to a predetermined, threshold concentration level of the chosen biomarker. Alternatively, the element 126 may include an electronic device configured to sense the biomarker. In such an embodiment where element 126 includes an electronic device, the electronic device may be configured to actuate an indicator such as an LED, or emit an odor, or produce an audible indication such as a periodic "beeping" sound, upon being exposed to the predetermined level of the biomarker. Accordingly, when the apparatus 100 has been used, an indicator, such as a change in the physical appearance, the smell, or the sound may be actuated or displayed. Therefore, an individual may look at, smell, or listen for the indicator of the element 126 to determine whether the apparatus 100 has been used.

It is noted that, despite the appearance of element 126 in FIGS. 1A and 1B, the depicted shape of a half crescent for the element 126 is intended to represent any or all of the embodiments of an element 126 that senses or is sensitive to a biomarker, such as $CO_2$, either directly or merely as a representation of an element that is accommodated in the detection unit 120. Thus, the half crescent shape of element 126 shown in FIG. 1B may represent a paper such as a material or cloth or an electronic device shaped to fit within the detection unit 120.

In an embodiment of the apparatus, in which the element 126 includes a material, the properties of the material may be such that the material changes color permanently upon exposure to a predetermined level of $CO_2$ or other biomarker. Thus, in this situation, a medical professional may be able to determine whether the apparatus 100 has been used by looking at the color of the material of the element 126 to see if the color has changed from the original state. For example, at the time of manufacture, the original color of the element 126 may be white. Then, after the apparatus 100 is used in a procedure and is thereby exposed to end tidal $CO_2$ or other biomarker, the element 126 may have turned red, as an indication that it has been used. Therefore, the individual would see the element 128 turned red and know that the apparatus was already used.

In an embodiment in which the element 126 is an electronic device, the electronic device may be embedded in the detection unit 120, for example in the chamber 124. The electronic device may have componentry sensitive to a biomarker, which upon exposure to the biomarker may perform any or more than one of the following actions: electrically connect an LED, trigger a switch to emit an odor, and/or trigger a switch to emit audible sound. Thus, multiple indicators may be combined to provide alternative ways of determining that the apparatus has been used. The electronic device may be powered by an internal power source embedded within the detection unit 120 or element 126, or the device may be powered by an external power source that may need to be connected or adjacent to the apparatus 100, for example via wireless power (power sources not explicitly depicted).

FIG. 1B is a cross-sectional view of the detection unit 120 along the line I-I shown in FIG. 1A. As previously mentioned, the detection unit 120 may include a chamber 124 with a hole 125 therethrough, and an element 126. Additionally FIG. 1B shows channel 128, which may be used to secure the breathing detection apparatus 100 to a nasal cannula 150 (seen in FIGS. 1C and 2). Channel 128 may be a passageway into the side of the detection unit 120 and may include a T-like shape having the ends of the "T" extend slightly toward the entrance of the channel 128 and away from the center of the detection unit 120. An individual may use the detection apparatus 100 to place a nasal cannula on either side of the T-like shape to secure the detection apparatus 100 to the nasal cannula. Alternatively, the channel 128 may include only one half of the T-like shape (not depicted), so as to appear similar to a candy cane shape. It is contemplated that other shapes for the channel 128 may be used to secure the detection apparatus 100 to a nasal cannula.

An advantage of using the T-like shape or the candy cane shape for the channel 128 is that after sliding the nasal cannula 150 into the channel 128, collar 130A may be connected to protrusion 122A, which in turn prevents nasal cannula 150 from being able to come out of the detection unit 120. That is, as seen in FIG. 1C, the passage 128 is blocked by collar 130, thereby preventing nasal cannula 150 from being accidentally removed.

It is noted that FIG. 1C and FIG. 1D are cross-sections of the apparatus 100 at lines II-II and respectively, shown in FIG. 1A.

Additional embodiments of various components shown in FIGS. 1A-1D are discussed herein below.

Figure 3A:
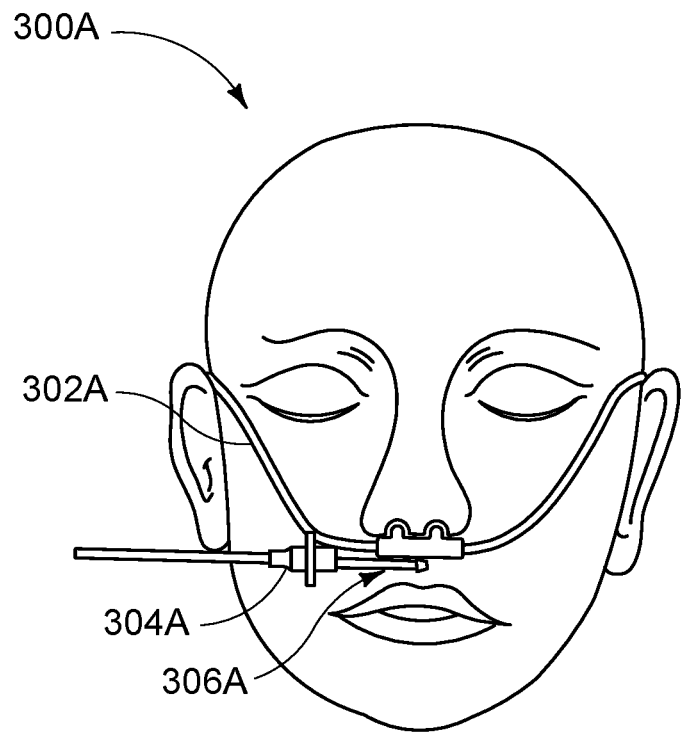
FIG. 3A illustrates an example breathing detection apparatus in use attached to a nasal cannula with the sampling tube attachment in position next to a patient's nose.
Figure 3B:
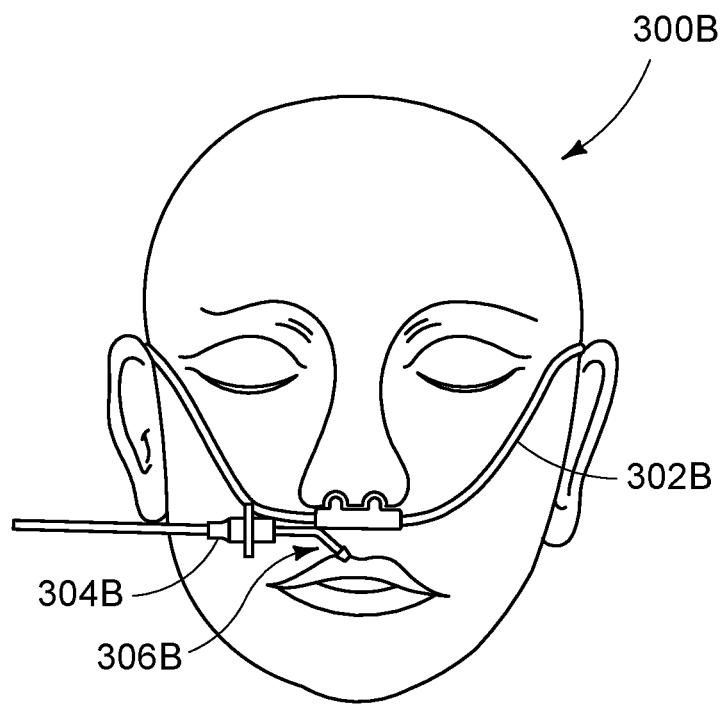
FIG. 3B illustrates an example breathing detection apparatus in use attached to a nasal cannula with the sampling tube attachment in position next to a patient's mouth.

FIG. 2 depicts the assembly 200 of detection apparatus 202 secured to a nasal cannula 204. As discussed above briefly, FIG. 3A depicts position 300A, where nasal cannula 302A is secured to a person and detection apparatus 304A is connected to the nasal cannula 302A. Further, the sampling tube attachment 306A is oriented closer to the nose than to the mouth of the patient. Alternatively, FIG. 3B depicts position 300B, where nasal cannula 302B is secured to a person and detection apparatus 304B is connected to the nasal cannula 302B. Note, however, that the sampling tube attachment 306B is oriented closer to the mouth than to the nose of the patient.

In FIG. 4, a patient is wearing a face mask depicting position 400. The mask 402 may include holes 404, and the detection apparatus 406 is depicted as connected to the mask 402 by way of inserting the distal end of the sampling tube attachment 408 into the mask 402 via flange 410 pushed through one of the holes 404. In this position 400, the width of the flange 410 is larger than the holes 404. Thus, the flange 410 is pushed through the holes 404 and the abutting end of the flange 410 minimizes the risk of accidental removal of the apparatus 406.

FIG. 5 depicts yet another alternative embodiment of position 500, in which the detection apparatus 514 is connected to an adapter 502 by way of inserting the flange 516 into a port 504 on the adapter 502. Furthermore, a first end 506 of the adapter 502 is connected to an endotracheal tube 510. A second end 508 of the adapter 502 is connected to an anesthesia circuit 512. Thus, the flange 516 is sized so as to be engageable with a port 504 of the adapter 502. Note that the collar 518 may be positioned on the port 504 also, so as to assist in securing the distal end of the sampling tube to the adapter 502.

Figure 6B:
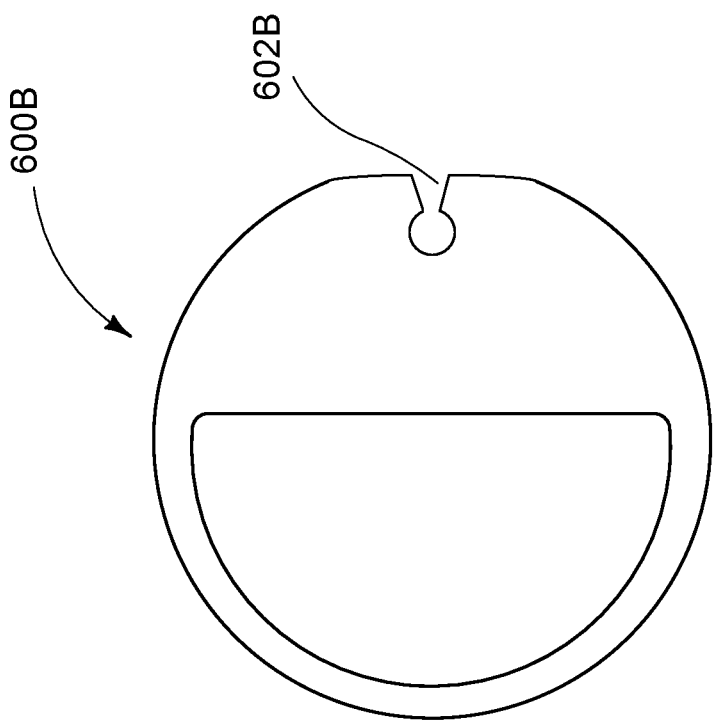
FIG. 6B illustrates another alternative example of a detection unit.
Figure 6A:
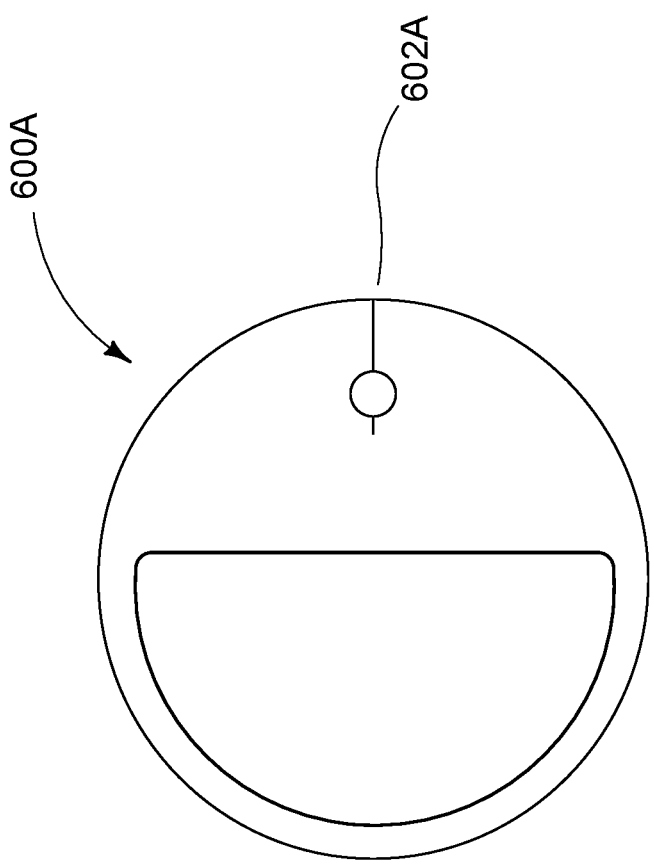
FIG. 6A illustrates an alternative example of a detection unit.

FIGS. 6A and 6B depict alternative embodiments of the detection unit 600A and 600B, respectively. For example, the detection unit 600A does not include a wide passageway from a side of the detection unit 600A to access channel 602A to insert a nasal cannula, as in FIG. 1B. Instead, the side of the detection unit 600A may be, for example, a slit, and the material of the detection unit 600A may be flexible so that unit 600A may be twisted to allow insertion of the nasal cannula. After twisting, the unit 600A will return to the original shape and the cannula should be held in place. Likewise, FIG. 6B shows detection unit 600B with a channel 602B having a width that is less than that of a nasal cannula. In this situation, the nasal cannula may be pinched to squeeze into the channel 602B until the channel opens wide enough for the nasal cannula. Notably, neither of the embodiments in FIGS. 6A and 6B would necessitate the collars 130A, 130B, as in FIG. 1A. Further, the protrusions 122A, 122B would also not be necessary.

As an alternative to the continuous tapering of flange 118 of FIG. 1 described above, the flange may be a cylinder-shaped flanged member 700A, (see FIG. 7A) having a nearly uniform outer width. Moreover, flange 700A may include an abutting end 702A, which may be orthogonal as shown in FIG. 1A and described above, or may be tapered inwardly toward the distal end of the first lumen 704A as shown in FIG. 7A, so as to form a ribbed anchor portion, which increases the force required to extract the tube since the ribbed anchor may spread out against the inner wall surface of a mask or port upon an attempt to extract the tube. Thus, the abutting end 702A creates greater surface area contact and greater resistance to extraction. Additionally, in the embodiment shown in FIG. 7A, the distal tip 706A thereof may be sloped or rounded slightly inward so as to ease insertion of the sampling tube attachment 708A into either a mask or a port, as described above.

Figure 7B:
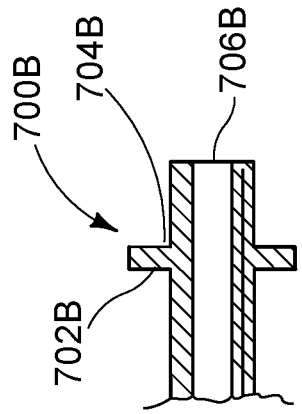
FIG. 7B illustrates another alternative example of a distal tip of the sampling tube attachment.
Figure 7A:
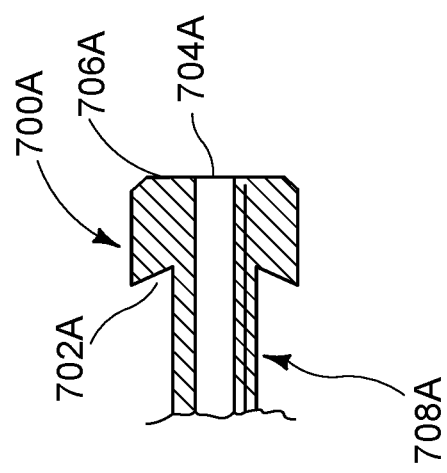
FIG. 7A illustrates an alternative example of a distal tip of the sampling tube attachment.

In yet another alternative embodiment depicted in FIG. 7B, the flange 700B may be a thin-walled, ring-shaped protrusion including an abutting end 702B and a distal end 704B that surrounds the first lumen 706B, either orthogonally to the axis of the first lumen 706B as shown in FIG. 7B, or angled forming a rib as described above, and is set a short way back from the distal tip. In this embodiment, the distal end of the first lumen 706B may be inserted into a mask or port, and then with some additional force applied, the flange 700B may flex backward against the outer wall of the mask or port so as to be pushed through the hole. Then, after passing through the hole, the flange 700B returns to the original position, such that the abutting end 702B abuts the inner wall of the mask or port, and restricts extraction.

Figure 8A:
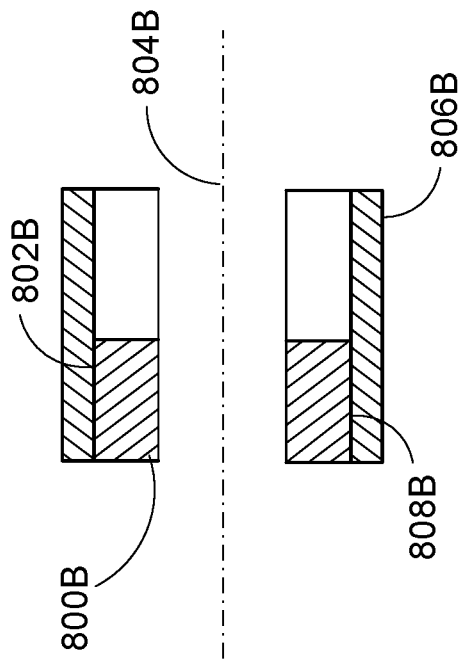
FIG. 8A illustrates an alternative example of a protrusion and collar.

In an alternative embodiment of the protrusions 122A, 122B from FIG. 1A, as seen in FIG. 8A, protrusion 800A (and the protrusion on the opposite side, not pictured) may include a lip flange 802A extending in a radial direction away from the axis of the first lumen 804A, instead of being threaded, as in FIG. 1A. Likewise, the collar 806A (and the collar on the opposite side, not pictured) may include a lip flange 808A extending radially inward toward the axis of the first lumen 804A. The lip flange 802A and lip flange 808A may be sized with respect to each other such that, upon pushing or pulling collar 806A against protrusion 800A, interference exists between opposing walls of the flanges 802A and 808A. In this manner, the collar 806A may be secured to the protrusion 800A via interference, instead of being threaded together. Furthermore, the thickness of the flange 802A in the "H" direction may be adjusted according to the rigidity properties of the material of the protrusion 800A or the lip flange 802A, (which elements may be integral or may form a composite of multiple pieces), so as to be sufficiently rigid to hold the collar 806A in place once connected, yet sufficiently flexible in order to allow the collar 806A to be pushed or pulled over the lip flange 802A under external force. Similarly, the thickness of the flange 808A in the "H1" direction may be adjusted according to the rigidity and elasticity properties of the material of the collar 806A or the lip flange 808A, (which elements may be integral or may form a composite of multiple pieces). Thus, upon pressing the lip flange 808A of the collar 806A against the lip flange 802A of the protrusion 800A, one or both of the lipped flanges 802A and 808A may flex under the applied force so as to allow the collar 806A to slide over the protrusion 800A and lock in place. After sliding into place, due to the elasticity of the materials, one or both of the lip flanges 802A and 808A then return to the original shape/position, such that opposing surfaces thereof are in abutment. Thusly, the protrusion 800A is engaged and locked with the collar 806A. One manner of achieving this embodiment may include selecting the appropriate materials for the protrusion 800A and the collar 806A. For example, the protrusion at 800A and the collar 806A may include rubber, plastic, or other suitable materials.

Figure 8B:
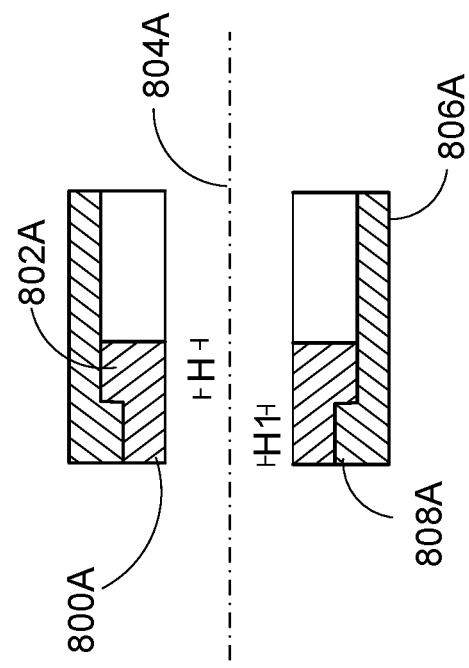
FIG. 8B illustrates another alternative example of a protrusion and collar.

In another alternative embodiment shown in FIG. 8B, protrusion 800B may have a smooth cylindrical outer surface 802B, and collar 806B may be hollow, having a smooth the interior surface 808B. Protrusion 800B and collar 806B are sized such that, when collar 806B is pushed toward protrusion 800B, outer surface 802B of protrusion 800B and interior surface 808B of collar 806B are in close contact, thereby creating an interference fit. The axis of the first lumen 804B passes between the protrusion 800B and the collar 806B. In order to ease insertion of protrusion 800B into collar 806B, the adjacent ends thereof may include a tapered edge. Therefore, in order to connect collar 806B to protrusion 800B, an operator may simply push the collar 806B onto the protrusion 800B.

CONCLUSION

Although several embodiments have been described in language specific to structural features and/or methodological acts, it is to be understood that the claims are not necessarily limited to the specific features or acts described. Rather, the specific features and acts are disclosed as illustrative forms of implementing the claimed subject matter.

What is claimed is:

1. A sampling apparatus, comprising:
a sampling tube to sample exhaled breath;
a housing into which the sampling tube transmits a sample of the exhaled breath, the housing including a slot disposed in a side of the housing such that when a cannula is laterally inserted into the slot, the cannula extends in a direction parallel to a direction of extension of the sampling tube; and
a collar that is connectable to the housing and is configured to be positioned in a connected position or a disconnected position,
wherein, when the collar is in the connected position, an external wall of the collar prevents removal of the cannula from the slot, and
wherein, when the collar is in the disconnected position, the cannula is insertable and/or removable from the slot.

2. The sampling apparatus according to claim 1, wherein the collar slides over the sampling tube to connect to the housing in the connected position.

3. The sampling apparatus according to claim 1, wherein the sample of the exhaled breath is carried to an end tidal $CO_2$ monitor device after passing through the housing.

4. The sampling apparatus according to claim 1, wherein the housing further includes a detection element that is sensitive to a systemic biomarker such that, upon exposure to a predetermined concentration level of the systemic biomarker, a state of the detection element experiences an alteration, thereby indicating that the predetermined concentration level of the systemic biomarker is present in the sample of the exhaled breath.

5. The sampling apparatus according to claim 4, wherein the detection element is sensitive to $CO_2$.

6. The sampling apparatus according to claim 1, wherein when the cannula is inserted into the slot and the collar is in the connected position, the collar does not deform a natural shape of the cannula.

7. The sampling apparatus according to claim 1, wherein the collar connects to the housing via a threaded engagement.

8. The sampling apparatus according to claim 1, wherein a direction of extension of the sampling tube is manually manipulable.

9. The sampling apparatus according to claim 1, wherein the slot extends inward into the housing from an outer edge of the housing before curving to extend back toward the outer edge of the housing.

10. A sampling system, comprising:
a sampling tube to sample exhaled breath;
a biomarker detection unit having a housing into which the sampling tube transmits a sample of the exhaled breath, the biomarker detection unit including:
a detection element disposed in a first portion of the housing to detect biomarkers in the exhaled breath, the first portion of the housing being formed of a transparent plastic, and
a slot disposed in a second portion of the housing that is adjacent to and integral with the first portion of the housing, the slot disposed such that when a cannula is laterally inserted into the slot, the cannula extends in a direction parallel to a direction of extension of the sampling tube; and
an obstruction element configured to be positioned in a connected position with the biomarker detection unit or in a disconnected position,
wherein, when the obstruction element is in the connected position, the obstruction element structurally prevents removal of the cannula from the slot without compression on the cannula, and
wherein, when the obstruction element is in the disconnected position, the cannula is insertable and/or removable from the slot.

11. The system according to claim 10, wherein the detection element is stored within a chamber in the first portion of the housing, the chamber being in fluid communication with the sampling tube.

12. The system according to claim 10, wherein the obstruction element is a collar that engages the housing of the biomarker detection unit.

13. The system according to claim 10, wherein upon exposure to a predetermined concentration level of a predetermined biomarker, the detection element experiences a permanent physical appearance alteration.

14. The system according to claim 10, further comprising a tip structure on a distal end of the sampling tube, the tip structure being sized to pass through a hole in a face mask under manual pressure, and the tip structure having a planar rear face with a perimeter sized larger than a largest dimension of the hole in the face mask such that, when the tip structure is inserted into the face mask, the planar rear face abuts an inside surface of the face mask surrounding the hole to prevent the sampling tube from falling out of the face mask.

15. The system according to claim 10, further comprising a tip structure on a distal end of the sampling tube, the tip structure being sized to pass through a port in an adapter for an endotracheal tube under manual pressure, and the tip structure having a planar rear face with a perimeter sized larger than a largest dimension of the port in the adapter for the endotracheal tube such that, when the tip structure is inserted into the port, the planar rear face abuts an inside surface of the port to prevent the sampling tube from falling out of the adapter for the endotracheal tube.

16. The system according to claim 10, wherein the slot divides into two branches that extend away from each other and transverse to the initial trajectory into the housing, each branch curving back to form a hook shape.

17. The system according to claim 16, wherein the obstruction element is configured to prevent removal of the cannula from both branches of the slot simultaneously.

18. The system according to claim 10, further comprising an extension tube that is in fluid communication with the biomarker detection unit to receive the sample of the exhaled breath from the sampling tube.

* * * * *